United States Patent [19]

Mustard

[11] 4,317,378

[45] Mar. 2, 1982

[54] LIQUID SAMPLING APPARATUS

[75] Inventor: Jack L. Mustard, Borger, Tex.

[73] Assignee: Phillips Petroleum Company, Bartlesville, Okla.

[21] Appl. No.: 161,109

[22] Filed: Jun. 19, 1980

[51] Int. Cl.³ .............................................. G01N 1/20
[52] U.S. Cl. ............................... 73/863.01; 73/863.52
[58] Field of Search ............ 73/863.02, 863.52, 863.53

[56] References Cited

U.S. PATENT DOCUMENTS

| 2,276,914 | 3/1942 | Atkinson | 73/863.02 |
| 2,316,537 | 4/1945 | Hendrickson | 73/863.02 |
| 3,625,064 | 12/1971 | Hinman, Jr. et al. | 73/863.52 |

Primary Examiner—S. Clement Swisher

[57] ABSTRACT

An improved liquid sampling device comprising a liquid trough having a liquid inlet end and a liquid discharge end with a liquid sample receptacle disposed below the liquid discharge end for receiving liquid samples through an open top portion of the liquid sample receptacle into the interior thereof. The liquid sample receptacle is rotatably supported below the liquid discharge end of the liquid trough whereby the liquid sample receptacle is rotatable between a first position with the open top portion thereof open to one side and a second position with the open top portion thereof open upwardly such that liquid falling into the open top portion from the liquid discharge end of the liquid trough is collected in the interior of the liquid sample receptacle. A first receptacle actuating device is provided for rotating the liquid sample receptacle from the first position to the second position thereof in response to the liquid falling from the liquid discharge end of the liquid trough, and a second receptacle actuating device is provided for rotating the liquid sample receptacle from the second position to the first position thereof in response to a reduction in the rate of liquid falling from the liquid discharge end of the liquid trough.

12 Claims, 5 Drawing Figures

LIQUID SAMPLING APPARATUS

This invention relates generally to improvements in liquid sampling apparatus. In one aspect the invention relates to a liquid sampling device for automatically sampling liquid from a liquid reservoir under reservoir overflow conditions.

Environmental considerations require the sampling of overflow from refinery wastewater sumps. Such overflow normally occurs during heavy rainstorms. To achieve such sampling, it is known to employ a liquid sample catcher consisting of a small steel box mounted on a sump overflow weir which catches overflow water and allows for automatic pumping from the box to a sample analysis station when the liquid level rises to a pre-set level in the sample catcher box. This apparatus employs a capacitance type probe to sense the liquid level in the box and start and stop a sample pump which is in fluid flow communication with the liquid in the box when it reaches a pre-set level. The sample catcher box is provided with holes in the bottom thereof which allow the box to drain and empty, thereby causing the sample pump to shut down when storm water overflow diminishes. After the sample catcher box is emptied, it is then ready to catch the required representative sample of the next sump overflow whenever it should occur.

The known sample catcher system is subject to certain operational problems. One of these problems is characterized by plugging of the holes in the bottom of the sample catcher box with sand or other debris which prevents the box from draining. After repeated rainstorm runoffs, such a sample catcher box has actually become filled with sand. As a result of this plugging of the sample catcher box drain holes, representative sampling is not obtained and the sample pump and sampler often become clogged with sand.

Another problem encountered with the sample catcher devices presently in use, is that durability and reliability of the capacitance level probes used therewith has been less than satisfactory.

The present invention contemplates a liquid sampling device comprising liquid conduit means having a liquid inlet end portion and a liquid discharge end portion for conducting liquid therethrough from the liquid inlet end portion toward the liquid discharge end portion. The device further includes liquid sample receptacle means disposed below the liquid discharge end portion of the liquid conduit means for receiving liquid samples through an open top portion of the liquid sample receptacle means into the interior of the liquid sample receptacle means, together with support means operatively related to the liquid sample receptacle means for rotatably supporting the liquid sample receptacle means below the liquid discharge end portion of the liquid conduit means. The device further includes first receptacle actuating means operatively related to the liquid sample receptacle means for rotating the liquid sample receptacle means from a first position thereof to a second position thereof in response to liquid falling from the liquid discharge end portion of the liquid conduit means; and second receptacle actuating means operatively related to the liquid sample receptacle means for rotating the liquid sample receptacle means from the second position thereof to the first position thereof in response to a reduction in the rate of liquid falling from the liquid discharge end portion of the liquid conduit means.

An object of the invention is to increase the efficiency of liquid sampling.

Another object of the invention is to increase the reliability of automatic liquid sampling.

A further object of the invention is to eliminate the adverse effects of sand and debris on the automatic operation of a liquid sampling device.

A still further object of the invention is to provide a liquid sampling device which is reliable and economical in construction and operation.

Other objects, aspects and advantages of the invention will be evident from the following detailed description when read in conjunction with the accompanying drawings in which.

Figure 4:
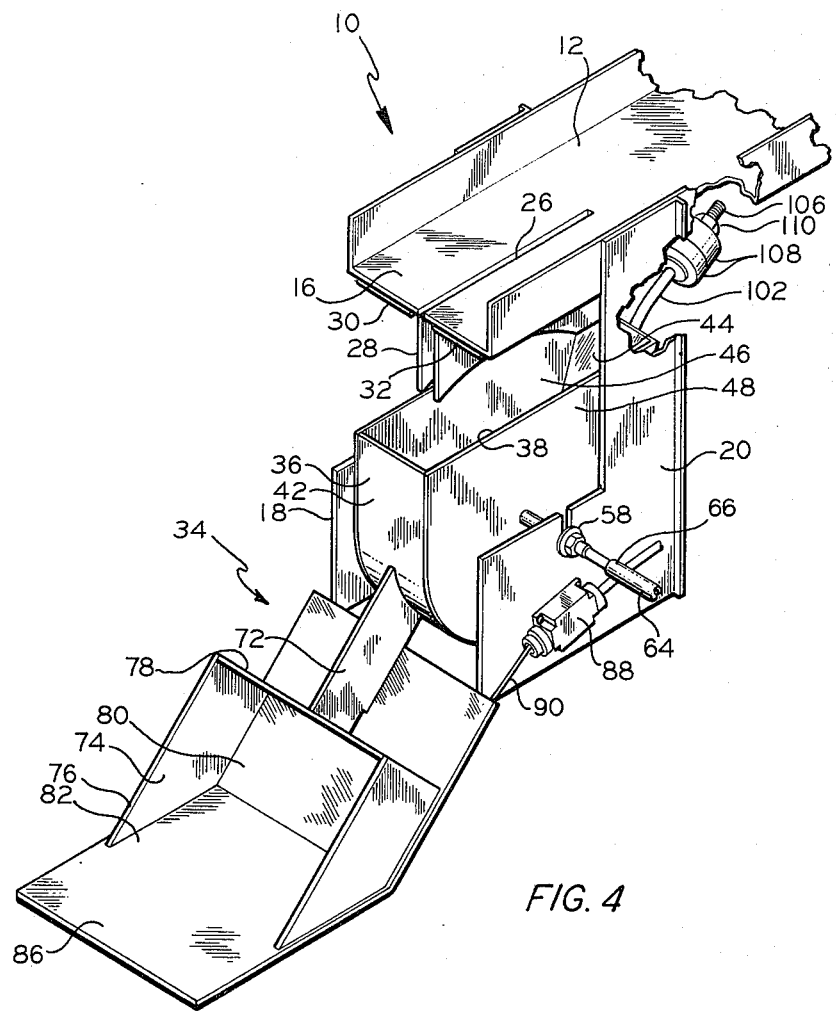
FIG. 4 is a partial, perspective view of the liquid sampling device of the present invention in the second sampling position thereof, with portions of the device broken away to more clearly illustrate the construction thereof.

Referring now to the drawings, a liquid sampling apparatus or device constructed in accordance with the present invention is illustrated therein and is designated by the reference character 10. The device 10 includes liquid conduit means in the form of a water overflow trough 12 having a liquid or water inlet end portion 14 and a liquid or water outlet end portion 16. A pair of L-shaped liquid sample receptacle support plates 18 and 20 are fixedly secured to an extend downwardly from the respective opposite sides of the water discharge end portion 16 of the trough 12. The plates 18 and 20 are provided with respective upwardly opening notches 22 and 24. A longitudinal slot 26 is formed in the water discharge end portion 16 of the trough 12 between the support plates 18 and 20. A shroud 28 extends downwardly from the water discharge end portion 16 of the trough 12. The shroud 28 is generally U-shaped when viewed in horizontal cross section and extends around the longitudinal slot 26. Both the longitudinal slot 26 and the shroud 28 are open at the outermost end of the water discharge end portion 16 of the trough 12, as best shown in FIG. 4. The lower surface of the outer end of the water discharge end portion 16 of the trough 12 is reinforced and protected by a pair of reinforcing elements 30 and 32, preferably formed of ⅜-inch square keystock welded to the underside of the trough 12. The trough 12 is preferably formed of a suitable length of 6-inch steel channel while the shroud 28 is preferably formed by a piece of No. 18 gauge type 304 or type 316 stainless steel sheet and each of the support plates 18 and 20 is preferably formed of No. 12 gauge type 304 or type 316 stainless steel plate. Securement between the trough 12 and the plates 18 and 20, shroud 28 and reinforcing elements 30 and 32 can be suitably achieved by welding.

Liquid sample receptacle means in the form of a liquid sample receptacle assembly 34 is supported beneath the water discharge end portion 16 of the trough 12 by means of the support plates 18 and 20. The liquid sample receptacle assembly 34 includes a liquid sample receptacle 36 having an open top portion 38, as viewed in FIGS. 2, 3 and 4. The interior of the liquid sample receptacle 36 communicates with the open top portion 38 and is defined by a generally circular bottom portion 40, a generally vertical front end portion 42, a generally upwardly and outwardly diverging rear end portion 44, and a pair of generally vertical, parallel sidewall portions 46 and 48.

Figure 3:
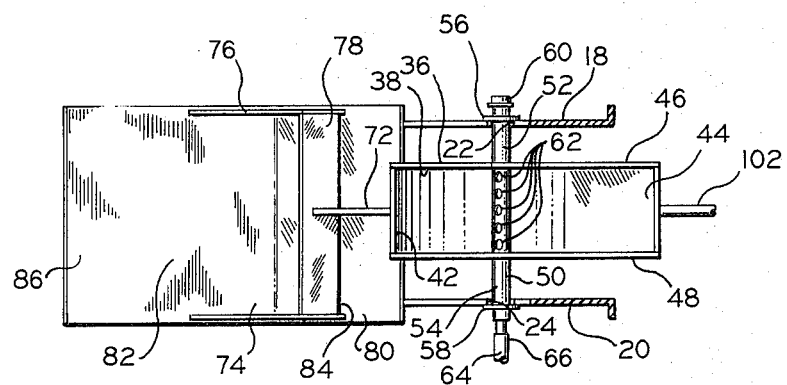
FIG. 3 is a partial, cross-sectional view taken along line 3—3 of FIG. 2.
Figure 5:
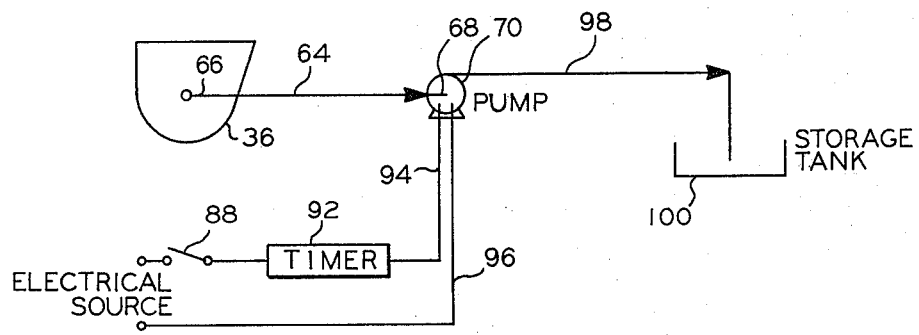
FIG. 5 is a schematic diagram illustrating both the liquid flow arrangement and electrical circuitry of the liquid sampling device of the present invention.

A tubular axle 50 extends through the sidewall portions 46 and 48 in perpendicular alignment therewith and is welded to the respective sidewall portions 46 and 48 to provide a liquid-tight seal therebetween. The first and second end portions 52 and 54 of the axle 50 are respectively pivotally supported in the notches 22 and 24 of the liquid sample receptacle support plates 18 and 20. Flanges 56 and 58 are fixedly secured respectively to the first and second end portions 52 and 54 of the axle 50 so as to center the liquid sample receptacle 36 between the support plates 18 and 20. The first end portion 52 of the tubular axle 50 is closed, preferably by means of a suitable threaded pipe cap as shown at 60. Five round apertures 62, preferably approximately ¼-inch in diameter, are formed in the wall of the tubular axle 50 between the sidewall portions 46 and 48 of the liquid sample receptacle 36, as best shown in FIG. 3. A flexible liquid conduit 64 is secured at a first end portion 66 thereof in fluid flow communication with the second end portion 54 of the tubular axle 50. The second end portion 68 of the conduit 64 is secured in fluid flow communication to the liquid inlet of a suitable pump 70, as illustrated schematically in FIG. 5. The flexible conduit 64 provides no significant restriction to the rotation of the liquid sample receptacle assembly 34.

Figures 1, 2:
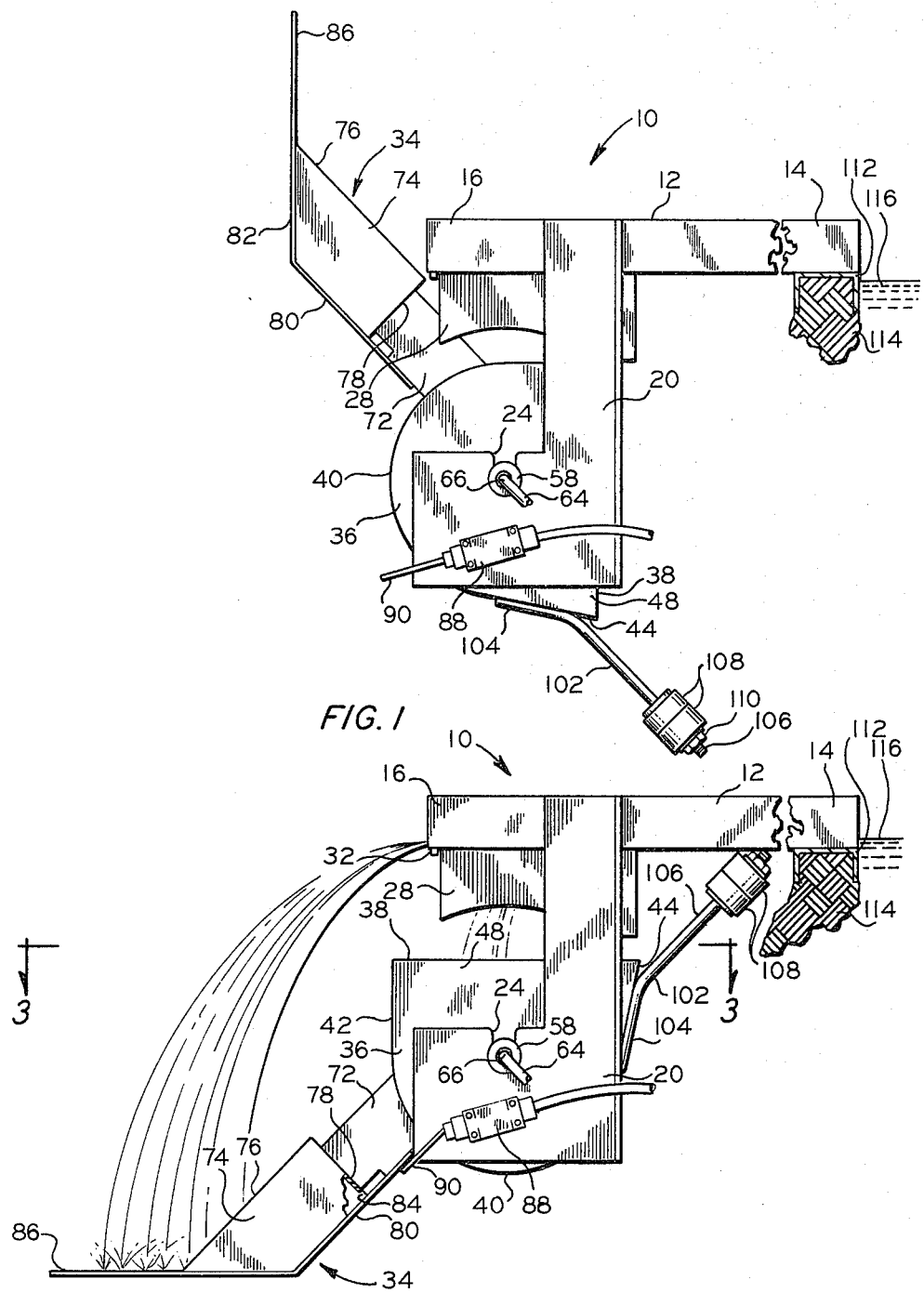
FIG. 1 is a side elevation view of a liquid sampling device constructed in accordance with the present invention in a first, non-sampling position thereof.
FIG. 2 is a side elevation view of the liquid sampling device of FIG. 1 in a second sampling position, with a portion broken away to illustrate construction details thereof.

A first receptacle actuating arm 72 is fixedly secured to the exterior surface of the generally circular bottom portion 40 of the liquid sample receptacle 36. A water or liquid catch bucket 74 is fixedly secured to the outer end of the first receptacle actuating arm 72. The catch bucket 74 has an open top portion 76. The catch bucket 74 further includes a back wall 78, a bottom wall 80 and an elongated front wall 82. The catch bucket 74 is further provided with an aperture 84, as best shown in FIG. 2, defined by the lower edge of the back wall 78 and the upper surface of the bottom wall 80. The outer end portion 86 of the elongated front wall 82 forms paddle means on the catch bucket 74 against which liquid or water impinges during the operation of the liquid sampling device 10, as will be described in detail hereinafter.

A limit switch 88 is mounted on the liquid sample receptacle support plate 20 with the switch actuator element 90 positioned to be engaged by the bottom wall 80 of the catch bucket 74 when the liquid sample receptacle assembly 34 is in the position illustrated in FIGS. 2 and 4. The limit switch 88 is preferably a normally open, single pole single throw switch interposed between one pole of an electrical source and a suitable timer device 92, as illustrated schematically in FIG. 5. The timer device 92 and the opposite pole of the electrical source are connected respectively by electrical conduits 94 and 96 to the electric drive motor of the pump 70. The liquid outlet of the pump 70 is connected via a suitable liquid conduit 98 to a liquid sample storage tank 100, as also schematically illustrated in FIG. 5.

A second receptacle actuating arm 102 is fixedly secured at the first end portion 104 thereof to the outer surface of the rear end portion 44 of the liquid sample receptacle 36. The second end portion 106 of the second receptacle actuating arm 102 is provided with one or more suitable counterweights 108 secured thereto by suitable means such as an internally threaded nut 110 threadedly engaged with the external threaded second end portion 106 of the second receptacle actuating arm 102. By carefully selecting the weight and position of the counterweights 108, the balance characteristics of the liquid sample receptacle assembly can be precisely adjusted for optimum performance.

In operation, the liquid sampling device 10 may be suitably secured to the weir or spillway 112 in a dam 114 of a water reservoir, such as a water sump for holding refinery wastewater or the like. During normal operations, the water level 116 of the water sump will be below the overflow level of the spillway 112, as shown in FIG. 1. Under these conditions, the counterweights 108 on the second receptacle actuating arm 102 retain the liquid sample receptacle assembly 34 in the first position thereof, as illustrated in FIG. 1. In this position, the open top portion 38 of the liquid sample receptacle 36 opens to one side so that any liquid in the liquid sample receptacle 36 drains therefrom along the rear end portion 44 thereof. The catch bucket 74 is positioned with the back wall 78 thereof adjacent the water discharge end portion 16 of the water overflow trough 12. In the event of water overflow over the level of the spillway 112, such as might be occasioned during a heavy rain storm, water would pass over the spillway 112 into the water inlet end portion 14 of the trough 12 and along the slightly downwardly inclined trough 12 where the water discharges from the water discharge end portion 16 of the trough 12 into the catch bucket 74. When the rate of water flow into the catch bucket 74 is sufficient to fill the catch bucket 74, in spite of the release of a small predetermined portion of such water through the aperture 84 in the catch bucket 74, the weight and momentum of the water flowing into the catch bucket 74 overcomes the counterbalance effect of the counterweights 108 on the second receptacle actuating arm 102, thus rotating the liquid sample receptacle assembly 34 from the first position illustrated in FIG. 1 to the second position illustrated in FIG. 2. The liquid sample receptacle assembly 34 will remain in the second position illustrated in FIG. 2 as long as water flows through the trough 12 at a sufficient flow rate to overcome the counterbalance effect of the counterweights 108. This is achieved by the momentum of the water discharging from the water discharge end portion 16 of the trough 12 and impinging upon the paddle structure of the outer end portion 86 of the catch bucket 74. While the liquid sample receptacle assembly is in the second position, any debris captured in the catch bucket 74 will be flushed away by the water impinging on the catch bucket.

It will be noted that when the liquid sample receptacle assembly 34 is being maintained in the second position illustrated in FIG. 2, the open top portion 38 of the liquid sample receptacle 36 is positioned directly below the slot 26 and the shroud 28 at the water discharge end portion 16 of the trough 12. Water passing through the trough 12 and downwardly through the slot 26 and shroud 28 flows directly into the interior of the liquid sample receptacle 36 to fill the liquid sample receptacle.

It will also be noted that when the liquid sample receptacle assembly 34 rotates to the second position thereof as shown in FIG. 2, the switch actuator element 90 of the limit switch 88 is contacted by the bottom wall 80 of the catch bucket 74, thus closing the limit switch 88 and applying current from the electrical source to the timer 92. The timer 92 is adjusted so as to provide a sufficient length of time for the liquid sample receptacle 36 to fill with sample water to a point above the apertures 62 in the tubular axle 50. Upon the passage of the predetermined sufficient length of time, the timer closes the circuit between the electrical source and the electric motor of the pump 70 thereby causing sample water to be withdrawn from the liquid sample receptacle 36 via conduit 64 and pumped to the sample storage tank 100 via conduit 98 for analysis of the content of the water sample or any other suitable operations on the water sample.

When water no longer flows through the trough 12 at a sufficient rate for the liquid sample receptacle assembly 34 to be maintained in the second position illustrated in FIG. 2 against the counterbalancing effect of the counterweights 108, the counterweights 108 cause the liquid sample receptacle assembly 34 to rotate back to the first position as illustrated in FIG. 1. At this time, contact is broken between the catch bucket 74 and the switch actuator element 90 of the limit switch 88 thereby opening the switch 88 and deactivating the pump 70. It will also be noted that any remaining liquid or water in the liquid sample receptacle 36 will be dumped therefrom along with any debris such as sand, rocks, twigs, leaves, etc. The specific configuration of the liquid sample receptacle 36, for example the employment of the upwardly and outwardly inclined rear end portion 44, causes the center of gravity of the liquid or water in the liquid sample receptacle 36 to shift to the right during the rotation from the second position of the liquid sample receptacle assembly 34 as viewed in FIG. 2 to the first position thereof as viewed in FIG. 1 thus assisting the counterbalancing effort of the counterweights 108 in returning the liquid sample receptacle assembly 34 to the first position thereof. The increased impetus given to the liquid sample receptacle assembly 34 by the shifting center gravity of the liquid in the liquid sample receptacle 36 causes the liquid sample receptacle assembly 34 to accelerate toward the first position thereof, thereby causing the catch bucket 74 to impact the water discharge end portion 16 of the trough 12 with force sufficient to dislodge any debris which may have found its way into either the liquid sample receptacle 36 or into the catch bucket 74.

It should also be understood that the shroud 28 functions to protect sample liquid falling through the slot 26 of the trough 12 into the liquid sample receptacle 36 from the adverse effects of wind when the liquid sample receptacle assembly 34 is in the second position illustrated in FIG. 2. The liquid sample receptacle assembly 34 can also be conveniently removed from the support plates 18 and 20 by merely lifting the end portions 52 and 54 of the axle 50 from the notches 22 and 24 of the support plates.

The liquid sample receptacle 36 and catch bucket 74 are preferably constructed of No. 18 gauge type 304 or 316 stainless steel sheet material, preferably assembled by welding as required. The first receptacle actuating arm 72 is preferably constructed of No. 12 gauge type 304 or type 316 stainless steel plate while the second receptacle actuating arm 102 is preferably formed of ½-inch diameter stainless steel bar stock.

From the foregoing description of the construction and operation of the liquid sampling device of the present invention, it will be seen that the present invention easily achieves the objects and advantages stated therefor. Changes may be made in the construction, combination and arrangement of parts or elements as heretofore set forth in the specification and shown in the drawings without departing from the spirit and scope of the invention as defined in the following claims.

That which is claimed is:

1. A liquid sampling device comprising:

liquid conduit means having a liquid inlet end portion and a liquid discharge end portion for conducting liquid therethrough from the liquid inlet end portion toward the liquid discharge end portion;

liquid sample receptacle means disposed below the liquid discharge end portion of said liquid conduit means for receiving liquid samples through an open top portion of said liquid sample receptacle means into the interior of said liquid sample receptacle means;

support means operatively related to said liquid sample receptacle means for rotatably supporting said liquid sample receptacle means below the liquid discharge end portion of said liquid conduit means whereby said liquid sample receptacle means is rotatable between a first position with the open top portion thereof open to one side, such that liquid drains from the interior through the open top portion of said liquid sample receptacle means, and a second position with the open portion thereof open upwardly such that liquid falling into the open top portion is collected in the interior of said liquid sample receptacle means;

first receptacle actuating means operatively related to said liquid sample receptacle means for rotating said liquid sample receptacle means from the first position thereof to the second position thereof in response to liquid falling from the liquid discharge end portion of said liquid conduit means at a predetermined rate and maintaining said liquid sample receptacle means in said second position for as long as liquid falls from the liquid discharge end portion of said liquid conduit means at a predetermined rate; and second receptacle actuating means operatively related to said liquid sample receptacle means for rotating said liquid sample receptacle means from the second position thereof to the first position thereof in response to a reduction of the rate of liquid falling from the liquid discharge end portion of said liquid conduit means below a predetermined rate and maintaining said liquid sample receptacle means in said first position for as long as liquid falls from the liquid discharge end portion of said liquid conduit means at less than a predetermined rate.

2. A liquid sampling device in accordance with claim 1 characterized further to include:

sample transfer means in fluid flow communication with the interior of said liquid sample receptacle means for transferring sample liquid away from said liquid sample receptacle means.

3. A liquid sampling device in accordance with claim 2 wherein said sample transfer means includes:

sample liquid conduit means having first and second end portions with the first end portion in fluid flow communication with the interior of said liquid sample receptacle means and with the second end portion at a location a distance from said liquid sample receptacle means, and having pump means interposed between the first and second end portions of said sample liquid conduit means for pumping sample liquid through said sample liquid conduit means from the first end portion toward the second end portion thereof.

4. A liquid sampling device in accordance with claim 3 wherein said sample transfer means further includes:
switch means operatively connected to said pump means and responsive to the position of said liquid sample receptacle means for activating said pump means when said liquid sample receptacle means is in the second position thereof and, alternately, for deactivating said pump means when said liquid sample receptacle means is in the first position thereof.

5. A liquid sampling device in accordance with claim 4 wherein said switch means includes:
timer means for delaying pumping of said sample liquid by said pump means for a predetermined time after said liquid sample receptacle means rotates to the second position thereof.

6. A liquid sampling device in accordance with claim 1 wherein said first receptacle actuating means includes:
liquid catch bucket means mounted on said liquid sample receptacle means so as to receive liquid discharged from the liquid discharge end portion of said liquid conduit means when said liquid sample receptacle means is in its first position, whereby the weight and momentum of liquid received by said liquid catch bucket means causes rotation of said liquid sample receptacle means and said liquid catch bucket means to the second position of said liquid sample receptacle means when the weight and momentum of liquid received by said liquid sample receptacle means reaches a predetermined value.

7. A liquid sampling device in accordance with claim 6 wherein said second receptacle actuating means includes:
counterbalance means connected to said liquid sample receptacle means so as to continuously urge said liquid sample receptacle means toward its first position.

8. A liquid sampling device in accordance with claim 6 or claim 7 wherein said liquid catch bucket means includes:

an aperture in the lower portion thereof when said liquid sample receptacle means is in its first position, said aperture being sized to permit liquid flow therethrough so as to regulate the speed with which said liquid catch bucket fills with liquid from said liquid conduit means; and
paddle means on said liquid catch bucket means for receiving liquid flow thereagainst from the liquid discharge end portion of said liquid conduit means when said liquid sample receptacle means is in its second position.

9. A liquid sampling device in accordance with claim 1 wherein:
said liquid sample receptacle means is rotatably supported on said support means by means of an axle having first and second end portions and extending through said liquid sample receptacle means with the first and second end portions of said axle supported by said support means.

10. A liquid sampling device in accordance with claim 9 wherein:
said axle is tubular and the first end portion of said axle is closed;
said axle includes at least one aperture therein intermediate the first and second end portions thereof and in fluid flow communication with the interior of said liquid sample receptacle means; and
the second end portion of said axle is in fluid flow communication with one end portion of sample liquid conduit means for conveying liquid from the interior of said liquid sample receptacle means therethrough via said tubular axle and the aperture therein.

11. A liquid sampling device in accordance with claim 1 wherein said liquid conduit means is characterized further to include:
a slot in the liquid discharge end portion of said liquid conduit means directly above said liquid sample receptacle means.

12. A liquid sampling device in accordance with claim 11 wherein said liquid conduit means is characterized further to include:
wind deflecting means disposed on opposite sides of said slot and extending downwardly therefrom toward said liquid sample receptacle means for facilitating the passage of liquid downwardly through said slot and into the interior of said liquid sample receptacle means when said liquid sample receptacle means is in the second position thereof.

* * * * *